United States Patent [19]

Sawicki

[11] Patent Number: 4,729,978

[45] Date of Patent: Mar. 8, 1988

[54] CATALYST FOR DEHYDRATION OF LACTIC ACID TO ACRYLIC ACID

[75] Inventor: Robert A. Sawicki, Stormville, N.Y.

[73] Assignee: Texaco Inc., White Plains, N.Y.

[21] Appl. No.: 45,633

[22] Filed: May 4, 1987

[51] Int. Cl.$^4$ .................. B01J 27/20; B01J 27/18; B01J 27/182; C07C 57/04
[52] U.S. Cl. .................. 502/174; 502/208; 502/214; 562/599
[58] Field of Search ............. 502/174, 176, 208, 214

[56] References Cited

U.S. PATENT DOCUMENTS

| | | | |
|---|---|---|---|
| 2,859,240 | 11/1958 | Holmen | 502/208 |
| 3,274,121 | 9/1966 | Schneider | 502/208 |
| 3,285,967 | 11/1966 | Schaeffer | 502/208 |
| 4,631,264 | 12/1986 | Hagen | 502/208 |

*Primary Examiner*—Paul E. Konopka
*Attorney, Agent, or Firm*—Robert A. Kulason; James J. O'Loughlin; Vincent A. Mallare

[57] ABSTRACT

A process for producing an acidic dehydration catalyst to convert lactic acid to acrylic acid. The process comprises impregnating an inert metal oxide carrier with a phosphate salt and buffering the impregnated carrier with a base to a pH sufficient to provide the effective dehydration catalyst.

12 Claims, No Drawings

CATALYST FOR DEHYDRATION OF LACTIC ACID TO ACRYLIC ACID

BACKGROUND OF THE INVENTION

This invention relates to catalysts useful in the preparation of acrylic acid from lactic acid. More particularly, it relates to the preparation of an acid dehydration catalyst to convert lactic acid to acrylic acid.

In the conversion of corn to useful chemicals, there have been various means and processes used to produce useful products such as those used in various chemical processes, surface coatings and textile industries.

The attempts converting lactic acid to acrylic acid by the use of traditional catalysts have been troubled with a problem of selectivity to acrylic acid. Generally, in these processes there has been the co-production of undesired acetaldehyde.

Thus, it is an object of this invention to provide a means for improving both the selectivity and productivity of acrylic acid from lactic acid with a minimum production of acetaldehyde.

DISCLOSURE STATEMENT

U.S. Pat. No. 2,859,240 discloses a process for producing acrylic acid and its lower alkyl esters from lactates by catalytic dehydration.

British Pat. No. 1,359,353 discloses a method of preparing an unsaturated acid or ester thereof by oxidizing an olefin with nitric acid.

SUMMARY OF THE INVENTION

The invention provides a process for preparing an acidic dehydration catalyst to convert lactic acid, selectively, to acrylic acid. The process comprises:
(a) impregnating an inert metal oxide carrier with a phosphate salt;
(b) buffering said impregnated carrier with a base to a pH ranging from about 5.2 to about 6.6; and
(c) recovering the catalyst.

The process is carried out at a temperature of about 200° C. to about 400° C. and the metal oxide carrier may be silica, titania or alumina.

DESCRIPTION OF THE INVENTION

According to the present invention, in connecting corn to a commodity chemical such as acrylic acid, the final step in the overall process is the catalytic dehydration of lactic acid to acrylic acid. In the conversion of corn to acrylic acid, the conventional sequence is:

CORN→glucose→lactic acid→ACRYLIC ACID

Commercially, the market for acylic acid and the acrylate esters is approximately two billion (2,000,000,000) pounds per year. These monomers are consumed primarily by the surface coatings and textile industries.

The use of traditional dehydration catalys* in terms of selectivity has been a problem of the co-production of acetaldehyde and formic acid which predominates in many instances, particularly when strong acidic catalysts are used.

According to the present invention, new and novel acidic dehydration catalysts have been found that are selective to acrylic acid. These catalysts as shown in the examples below are selective to the production of acrylic acid and minimize the co-production of acetaldehyde to an amount which will not effect the quality and yield of the desired product of acrylic acid.

According to the present invention, the acidic dehydration catalyst to convert lactic acid to acrylic acid is prepared by initially impregnating an inert metal oxide carrier with a phosphate salt, then buffering the impregnated carrier with a base to a pH ranging from about 5.2 to about 6.6 and finally, recovering the dehydration catalyst.

The optimum and preferred pH is about 5.9 and the temperature under which the process to convert lactic acid to acrylic acid is carried out at a temperature of about 200° C. and about 400° C. The preferred temperature is about 350° C.

The metal oxide carrier may be selected from the group consisting of silica, titania and alumina. The preferred metal oxide is silica.

The phosphate salt that is used according to the present invention may be selected from the group consisting of sodium dihydrogen phosphate ($NaH_2PO_4$), sodium hydrogen phosphate ($Na_2HPO_4$), potassium hydrogen phosphate ($K_2HPO_4$), potassium dihydrogen phosphate ($KH_2PO_4$), lithium hydrogen phosphate ($Li_2HPO_4$), lithium dihydrogen phosphate ($LiH_2PO_4$), lanthanum phosphate ($LaPO_4$), magnesium phosphate [$Mg_3(PO_4)_2$] and calcium dihydrogen phosphate [$Ca(H_2PO_4)_2$]. The preferred phosphate is sodium dihydrogen phosphate ($NaH_2PO_4$).

The base material may be selected from the group consisting of $Na_2CO_3$, $NaHCO_3$, $KHCO_3$, $K_2CO_3$, $LiCO_3$, $CaCO_3$, $MgCO_3$ and $La_2(CO_3)_3$.

In impregnating the metal oxide carrier such as silica, the amount of phosphate salt used is about 0.1 to about 10.0 mmoles per gram of carrier or support. The preferred amount of phosphate salt is about 1.0 mmole per gram of carrier.

In converting lactic acid to acrylic acid, it is important to note that the number and strength of the acid sites on the surface of the heterogeneous catalyst appears to influence the selectivity and productivity to acrylic acid. A pH value either too high or too low appears to favor the formation of acetaldehyde. By using the dehydration catalyst produced by the present invention, the optimum yield of acrylic acid with a minimum production of acetaldehyde results.

The relationship between catalyst pH and its activity was demonstrated by the preparation and evaluation of a variety of materials. Such evaluation and comparison of materials is illustrated below in the following examples and Tables I, II and III.

EXAMPLES I-XIII

In the examples, the pH was measured prior to impregnation and the activity compared. The pH values were measured with a pH meter as an aqueous solution prior to impregnation onto the silica spheres of the carrier. The results are recorded for the first four (4) examples below in Table I.

TABLE I

MODIFIED SODIUM DIHYDROGEN PHOSPHATE ON SILICA CATALYSTS

| Example | Reagent | pH Value | Conv. % | Acrylic Acid Select % | Acrylic Acid Yield % | Acetaldehyde Select % | Acetaldehyde Yield % |
|---|---|---|---|---|---|---|---|
| I | — | 4.4 | 94 | 30 | 28 | 56 | 53 |
| II | $NaHSO_4$ | 2.8 | 96 | 13 | 12 | 57 | 55 |
| III | $Na_2SO_4$ | 4.4 | 95 | 28 | 27 | 37 | 35 |

TABLE I-continued
MODIFIED SODIUM DIHYDROGEN PHOSPHATE ON SILICA CATALYSTS

| Example | Reagent | pH Value | Conv. % | Acrylic Acid Select % | Acrylic Acid Yield % | Acetaldehyde Select % | Acetaldehyde Yield % |
|---|---|---|---|---|---|---|---|
| IV | NaHCO$_3$ | 5.6 | 88 | 43 | 37 | 25 | 22 |

As can be seen in Table I, lowering the pH with an acidic component (Example II) gave a less selective catalyst, the addition of a neutral material (Example III) had little effect and the addition of a basic reagent (Example IV) markedly improved both the activity and selectivity to acrylic acid.

The relationship between the activity and catalyst pH was further examined by the addition of varying mole percentages of base to the standard phosphate catalyst. The results of such examination for the next eight (8) examples are recorded below in Table II.

TABLE II

| Example | NaHCO$_3$ (mole %) | pH | Conv. % | Acrylic Acid Select % | Acrylic Acid Yield % | Acetaldehyde Select % | Acetaldehyde Yield % |
|---|---|---|---|---|---|---|---|
| V | 0 | 4.4 | 94 | 30 | 28 | 56 | 53 |
| VI | 10 | 5.2 | 89 | 38 | 34 | 43 | 38 |
| VII | 15 | 5.5 | 86 | 36 | 31 | 21 | 18 |
| VIII | 20 | 5.7 | 88 | 43 | 37 | 25 | 22 |
| IX | 25 | 5.8 | 82 | 41 | 34 | 22 | 18 |
| X | 30 | 9.9 | 85 | 49 | 42 | 29 | 24 |
| XI | 40 | 6.2 | 77 | 56 | 43 | 36 | 28 |
| XII | 60 | 6.6 | 79 | 50 | 39 | 41 | 32 |

As shown in Table II, an optimum value of approximately 30 mole % (pH=5.9) of bicarbonate was obtained. This catalyst gave the highest percentage of acrylic with the least amount of acetaldehyde.

A further improvement in this thermal dehydration process was shown and is claimed to be the use of the sequential addition technique in catalyst preparation. As recorded in Table III below, it is shown that the catalyst could be improved further by the sequential addition of the reagents to the catalyst carrier where first the phosphate salt is impregnated and then the resulting composition is treated with an aqueous basic solution. Example X was prepared by impregnation of silica with an aqueous mixture containing the two salts, sodium dihydrogen phosphate and sodium bicarbonate. Example XIII was prepared by the initial impregnation of phosphate onto the silica followed by, after drying, the impregnation of bicarbonate. By the results shown in Table III below, it can be assumed that this technique gives a greater number of active sites on the surface of the catalyst and that the bicarbonate may also help neutralize some of the acidic sites on the catalyst carrier.

TABLE III

| Example | % Conv | Acrylic Acid % Select | Acrylic Acid % Yield | Acetaldehyde % Select | Acetaldehyde % Yield |
|---|---|---|---|---|---|
| X | 89 | 49 | 42 | 29 | 24 |
| XIII | 89 | 65 | 58 | 17 | 15 |

Thus, in view of the results set forth above in the tables, according to the present invention an effective dehydration catalyst is available to selectively and actively convert lactic acid to acrylic acid.

EXPERIMENTAL SECTION

All reactions were performed with reagents of the highest purity commercially available. The pyrolysis of lactic acid was accomplished using a vertical furnace oven, pyrex tube and syringe pump. Typically, 50 cc of catalyst was used and the dead space filled with glass beads to act as pre and post heaters. The lactic acid feed contained 0.3 wt. % hydroquinone as a polymerization inhibitor. The reaction was run downflow with either a nitrogen or argon gas blanket. The products were collected in a cold trap and quantified by high performance liquid chromatography (HPLC).

Example I; a mixture containing 27.6 g (0.2 moles) of sodium dihydrogen phosphate monohydrate, 140 ml water and 200 g silica spheres (United Catalysts Inc., T-1571) was stirred on a rotary evaporator at room temperature for 2 hours. Subsequent drying at 100° C. under water aspirator vacuum yielded white spheres which were dried in a vacuum oven overnight at 100° C.

Examples II-IV, Table I; a mixture containing 30 moles sodium dihydrogen phosphate monohydrate, 5 mmoles reagent and 25 ml water was stirred and the pH value measured using a pH meter. Silica (30 g) was added and the mixture impregnated by evaporation and drying. Catalyst prepared in a similar manner are reported in Table II as well, Examples V-XII, using 0-60 mole % of sodium bicarbonate as the reagent.

The catalyst preparation in Example XIII represents the best mode known of practicing the method of this invention. The catalyst used was prepared as follows: A mixture containing 32 g of the standard phosphate catalyst (Example V), 0.75 g (9 mmoles) sodium bicarbonate and 25 ml water was stirred 2 hours at room temperature and dried in the usual manner.

In Examples I-XIII the catalyst evaluation and dehydration of an aqueous lactic acid solution to acrylic acid followed the general procedure reported in Tables I-III. The values obtained for lactic acid conversion (Conv.), selectivity (Select) and yield to both acrylic acid and acetaldehyde are based on standard analytical methods using high performance liquid chromatography (HPLC).

The following described general procedure for dehydrating lactic acid was used in each experiment.

A lactic acid solution (20%) in water with hydroquinone (0.3 wt. %) was added (45 ml), via syringe, to the top of a heated (350° C.) pyrex tube containing 50 cc of catalyst. An inert gas was used (20 ml/min) and the liquid flow rate was 0.34 ml/min. The effluent was collected in a series of cold traps and the products quantified using HPLC.

The present invention as described above may be modified in many ways by those of ordinary skill in the art without departing from the scope of the invention as set forth in the appending claims.

We claim:
1. A process for preparing an acidic dehydration catalyst to convert lactic acid to acrylic acid, said process comprising the steps of:
   (a) impregnating an inert metal oxide carrier with a phosphate salt;
   (b) buffering said impregnated carrier with a base to a pH ranging from about 5.2 to about 6.6; and
   (c) recovering the catalyst.

2. The process of claim 1, wherein said inert metal oxide is selected from the group consisting of silica, titania and alumina.

3. The process of claim 1, wherein said phosphate salt is selected from the group consisting of $NaH_2PO_4$, $Na_2HPO_4$, $K_2HPO_4$, $KH_2PO_4$, $Li_2HPO_4$, $LiH_2PO_4$, $LaPO_4$, $Mg_3(PO_4)_2$ and $Ca(H_2PO_4)_2$.

4. The process of claim 1, wherein said base is selected from the group consisting of $Na_2CO_3$, $NaHCO_3$, $KHCO_3$, $K_2CO_3$, $LiCO_3$, $CaCO_3$, $MgCO_3$ and $La(CO_3)_3$.

5. The process of claim 1, wherein said pH is about 5.9.

6. The process of claim 1, wherein said process is carried out at a temperature of about 200° C. to about 400° C.

7. The process of claim 1, wherein said carrier is impregnated with an amount of about 0.1 to about 10.0 m moles of phosphate salt per gram of carrier.

8. The process of claim 7, wherein the amount of phosphate salt is about 1.0 mmole per gram of carrier.

9. The process of claim 2, wherein said inert metal oxide is silica.

10. The process of claim 3, wherein said phosphate salt is sodium dihydrogen phosphate.

11. The process of claim 4, wherein said base is $NaHCO_3$.

12. The process of claim 6, wherein said temperature is about 350° C.

* * * * *